US010176603B2

United States Patent
Rigie et al.

(10) Patent No.: US 10,176,603 B2
(45) Date of Patent: Jan. 8, 2019

(54) SINOGRAM (DATA) DOMAIN PANSHARPENING METHOD AND SYSTEM FOR SPECTRAL CT

(71) Applicants: THE UNIVERSITY OF CHICAGO, Chicago, IL (US); TOSHIBA MEDICAL SYSTEMS CORPORATION, Otawara-Shi, Tochigi-Ken (JP)

(72) Inventors: David Rigie, Chicago, IL (US); Patrick La Riviere, Chicago, IL (US); Adam Petschke, Lake Bluff, IL (US); Yuexing Zhang, Naperville, IL (US)

(73) Assignees: The University of Chicago, Chicago, IL (US); Toshiba Medical Systems Corporation, Otawara-shi (JP)

( * ) Notice: Subject to any disclaimer, the term of this patent is extended or adjusted under 35 U.S.C. 154(b) by 202 days.

(21) Appl. No.: 13/960,821

(22) Filed: Aug. 7, 2013

(65) Prior Publication Data
US 2015/0043796 A1    Feb. 12, 2015

(51) Int. Cl.
*A61B 6/00*      (2006.01)
*G06T 11/00*   (2006.01)
(Continued)

(52) U.S. Cl.
CPC .......... *G06T 11/005* (2013.01); *A61B 6/4241* (2013.01); *G06T 3/4061* (2013.01); *G06T 5/003* (2013.01); *G06T 2211/408* (2013.01)

(58) Field of Classification Search
CPC ............. G06T 2207/10036; G06T 5/50; G06T 2207/10041; G06T 11/005; G06T 7/0083;
(Continued)

(56) References Cited

U.S. PATENT DOCUMENTS 5,949,914 A  *  9/1999  Yuen ........................... 382/254
6,858,849 B2 *  2/2005  Yamashita ............. A61B 6/037
                                                                    250/363.03
(Continued)

FOREIGN PATENT DOCUMENTS

WO    2012/056412 A1    5/2012
WO    2012/123845 A1    9/2012

OTHER PUBLICATIONS

Fang et al., A Variational Approach for Pan-Sharpening, Jul. 2013 [retrieved Dec. 3, 2015], IEEE Transactions on Image Processing, vol. 22, No. 7, pp. 2822-2834. Retrieved from the Internet: http://ieeexplore.ieee.org/xpls/abs_all.jsp?arnumber=6502715&tag=1.*

(Continued)

*Primary Examiner* — Andrew Moyer
*Assistant Examiner* — Dennis Rosario
(74) *Attorney, Agent, or Firm* — Kenichiro Yoshida

(57) ABSTRACT

A hybrid CT dataset is obtained from a combination of an integrating detector and a photon-counting detector. The hybrid CT dataset contains sparse spectral energy data and dense energy integration data. The dense panchromatic data sets inherit the resolution properties of the integrating detector while the sparse spectral data sets inherit the spectral information of the photon-counting detector. Subsequently, the sparse spectral energy data sets are pansharpened based upon at least one dense panchromatic data set that lacks spectral information according to a pansharpening algorithm.

17 Claims, 9 Drawing Sheets

(51) Int. Cl.
  *G06T 5/00* (2006.01)
  *G06T 3/40* (2006.01)
(58) Field of Classification Search
  CPC ... G06T 7/0012; G06T 7/0089; G06T 7/0081;
    G06T 2207/10081; G06T 2211/436;
    G06T 2211/408; G06T 2207/20221;
    G06T 5/003; G06T 3/4061; G06K
    9/0063; A61B 6/032; A61B 6/037; A61B
    6/4241; A61B 6/482; G01N 23/046
  See application file for complete search history.

(56) References Cited

U.S. PATENT DOCUMENTS

| | | | | |
|---|---|---|---|---|
| 7,433,443 | B1* | 10/2008 | Tkaczyk | A61B 6/032 378/19 |
| 7,450,683 | B2* | 11/2008 | Tkaczyk | A61B 6/032 250/370.08 |
| 7,573,040 | B2* | 8/2009 | Tkaczyk | G01T 1/249 250/370.09 |
| 7,606,347 | B2* | 10/2009 | Tkaczyk | A61B 6/032 378/19 |
| 7,796,153 | B1* | 9/2010 | Sanderson et al. | 348/145 |
| 9,069,092 | B2* | 6/2015 | Oreper | G01T 1/2985 |
| 9,224,216 | B2* | 12/2015 | Zamyatin | G06T 7/0012 |
| 9,285,326 | B2* | 3/2016 | Gagnon | A61B 6/032 |
| 2013/0284939 | A1* | 10/2013 | DeMan | A61B 6/032 250/393 |

OTHER PUBLICATIONS

Piella, Image Fusion for Enhanced Visualization: A Variational Approach, Jun. 2009 [retrieved Dec. 3, 2015], International Journal of Computer Vision, vol. 83, Issue 1, pp. 1-11. Retrieved from the Internet: http://link.springer.com/article/10.1007/s11263-009-0206-4.*

Socolinsky et al., Multispectral Image Visualization Through First-Order Fusion, Aug. 2002 [retrieved Dec. 3, 2015], IEEE Transactions on Image Processing, vol. 11, No. 8, pp. 923-931. Retrieved from the Internet: http://ieeexplore.ieee.org/xpls/abs_all.jsp?arnumber=1025166&tag=1.*

Rigie et al., Variational noise reduction for spectral CT: Insights from the perspective of multiresolution image fusion, Oct. 2013 [retrieved Sep. 4, 2017], Conference Paper: 2013 IEEE Nuclear Science Symposium and Medical Imaging Conference Record, 3 pages total.*

Website titled: TH-A-103-07: A Pan-Sharpening Approach to Multiresolution Image Fusion for Hybrid Counting/ Integrating CT. Retrived from the Internet Sep. 4, 2017: http://onlinelibrary.wiley.com/doi/10.1118/1.4815724/abstract?crawler=true.*

Kim et al., An Asynchronous Sampling-Based 128×128 Direct Photon-Counting X-Ray Image Detector with Multi-Energy Discrimination and High Spatial Resolution, Dec. 3, 2012 [retrieved Apr. 13, 2018], IEEE Journal of Solid-State Circuits, vol. 48, Issue 2, pp. 541-558. Retrieved from the Internet: https://ieeexplore.ieee.org/abstract/document/6373763/.*

Rigie et al., TH-A-103-07: A Pan-Sharpening Approach to Multiresolution Image Fusion for Hybrid Counting/integrating CT, Jun. 2013 [retrieved Aug. 21, 2018], Medical Physics, vol. 40, No. 6, p. 527. Retrieved from the Internet: https://public.nlm.nih.gov/projects/relais/1252852.pdf.*

Zhou et al., Panchromatic and Multi-spectral Image Fusion Using IHS and Variational Models, Oct. 16-18, 2012 [retrieved Aug. 21, 2018], 2012 5th International Congress on Image and Signal Processing, pp. 1077-1080. Retrieved from the Internet: https://ieeexplore.ieee.org/abstract/document/6469990/.*

Edward W. Mowle and Cornelius J. Dennehy, The Landsat-6 Satellite: An Overview, Telesystems Conference, 1991. Proceedings, Mar. 26-27, 1991, pp. 277-282, vol. 1, IEEE, Atlanta, GA.

Coloma Ballester, et al., A Variational Model for P+XS Image Fusion, International Journal of Computer Vision 69, Apr. 2006, pp. 43-58, No. 1, Spring Science + Business Media, LLC., The Netherlands.

Zeming Zhou, et al., Pan-sharpening: a Fast Variational Fusion Approach, Science China Information Sciences, Mar. 2012, pp. 615-625, vol. 55 No. 3, Science China Press and Springer-Verlag Berlin Heidelberg.

Patrick J. La Riviere, et al., Penalized-Likelihood Sinogram Restoration for Computed Tomography, Ieee Transactions on Medical Imaging, Aug. 2006, pp. 1022-1036, vol. 25 No. 8, IEEE, Iowa City, IA.

* cited by examiner

SINOGRAM (DATA) DOMAIN PANSHARPENING METHOD AND SYSTEM FOR SPECTRAL CT

FIELD OF THE INVENTION

The current invention is generally related to computer tomography (CT) image processing, and more particularly related to pansharpening of CT sparse spectral sinogram using a dense panchromatic (non-spectral) sinogram.

BACKGROUND OF THE INVENTION

There is great desire to incorporate photon-counting detectors also known as energy discriminating X-ray detectors in computed tomography (CT). The photon-counting detectors have some potential to improve image quality, reduce dose and enable new clinical applications of CT. The photon-counting detectors acquire data including extra spectral information for providing material classification, improving quantitative imaging and reducing beam-hardening artifacts.

Despite the above advantages over widely used energy-integrating detectors, the photon-counting detectors have certain disadvantages. The photon-counting detectors are generally limited by the high costs and their count-rate. Furthermore, although the signal-to-noise ratio (SNR) in the photon-counting detectors is reduced at low flux levels for a small pixel size, the photon-counting detectors experience an increased level of inter-pixel interference due to the small pixel size. On the other hand, the photon-counting detectors such as CdTe/CdZnTe sensors have poor performance at high flux levels, and consequently the SNR deteriorates. For these reasons, the photon-counting detectors have not yet replaced the energy-integrating detectors currently utilized in clinical CT systems.

Because of the above described issues of the photon-counting detectors, a dual-tube CT system has been proposed to utilize a combination of photon-counting detectors and integrating detectors. In one exemplary dual-tube CT system, one source projects X-ray towards a photon-counting detector while the other source projects X-ray towards a conventional detector that is placed at a predetermined angle with respect to the photon-counting detector. In order to cope with the high flux rates used in the exemplary dual-tube CT system, the pixel-size of the photon-counting detector was made substantially small, but charge sharing and K-escape rates have been increased to a point where the above described advantages of the photon-counting detector have substantially diminished.

Because of the above described prior art, there remains a desire to improve CT imaging using photon-counting detectors without suffering from the known disadvantages such as the high cost and the low sampling rate.

DETAILED DESCRIPTION OF THE PREFERRED EMBODIMENT(S)

Figure 1:
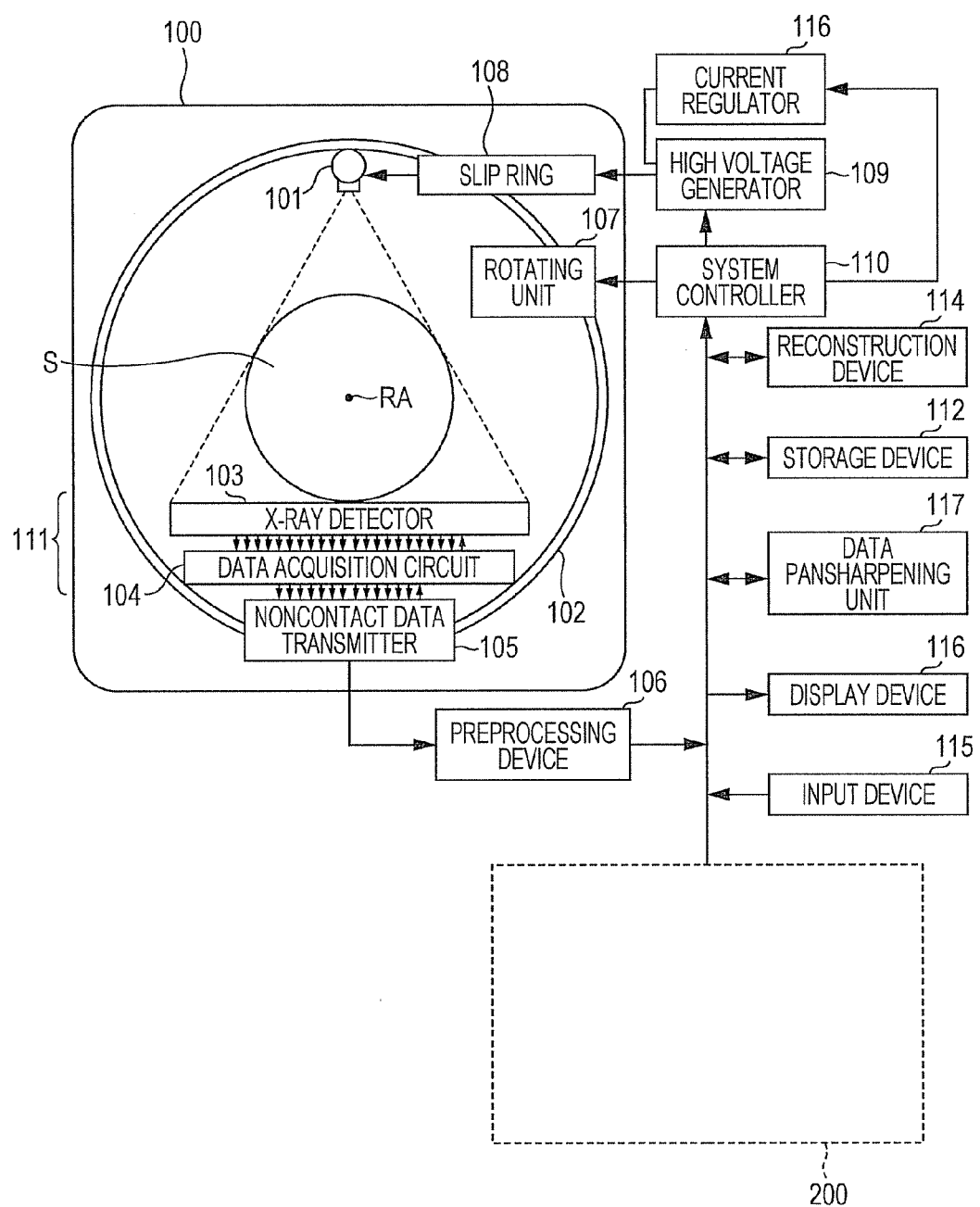
FIG. 1 is a diagram illustrating one embodiment of the multi-slice X-ray CT apparatus or scanner for pansharpening a sparse spectral data set according to the current invention.

Referring now to the drawings, wherein like reference numerals designate corresponding structures throughout the views, and referring in particular to FIG. 1, a diagram illustrates one embodiment of the multi-slice X-ray CT apparatus or scanner for pansharpening a sparse spectral data set according to the current invention including a gantry 100 and other devices or units. The gantry 100 is illustrated from a front view and further includes an X-ray tube 101, an annular frame 102 and a multi-row or two-dimensional array type X-ray detector 103. The X-ray tube 101 and X-ray detector 103 are diametrically mounted across a subject S on the annular frame 102, which rotates around axis RA. Although a single pair of the X-ray tube 101 and X-ray detector 103 is illustrated in the diagram, the embodiment for pansharpening a sparse spectral data set optionally includes more than a single pair of the X-ray tube 101 and X-ray detector 103. A rotating unit 107 rotates the frame 102 at a high speed such as 0.4 sec/rotation while the subject S is being moved along the axis RA into or out of the illustrated page.

The multi-slice X-ray CT apparatus further includes a high voltage generator 109 that applies a tube voltage to the X-ray tube 101 so that the X-ray tube 101 generates X ray. In one embodiment, the high voltage generator 109 is mounted on the frame 102. The X rays are emitted towards the subject S, whose cross sectional area is represented by a circle. The X-ray detector 103 is located at an opposite side from the X-ray tube 101 across the subject S for detecting the emitted X rays that have transmitted through the subject S.

Still referring to FIG. 1, the X-ray CT apparatus or scanner further includes a data acquisition device 111 for detecting the emitted X rays and processing the detected signals. In one embodiment, the X-ray detector 103 is implemented using photon counting detectors for counting photons in each of a predetermined number of energy bins. Each of the energy bins defines a predetermined range of energy in the transmitted X-ray at the detector 103. Furthermore, the X-ray detector 103 is implemented using a combination of photon-counting detectors and energy-integrating detectors. After detecting the emitted X rays at the X-ray detector 103, a data acquisition circuit 104 converts a signal output from the X-ray detector 103 for each channel into a voltage signal, amplifies it, and further converts it into a digital signal. The X-ray detector 103 and the data acquisition circuit 104 are configured to handle a predetermined total number of projections per rotation (TPPR).

In one embodiment of pansharpening spectral data according to the current invention, the X-ray detector 103 includes a combination of photon-counting detectors and energy-integrating detectors. The photon-counting detectors detect sparse spectral data while the energy-integrating detectors detect dense panchromatic (non-spectral) data. Although one exemplary configuration of the photon-counting detectors and the energy-integrating detectors will be illustrated in another embodiment with respect to FIG. 2, the current invention as recited in the appended claims is not necessarily limited to a specific geometric configuration and includes variations.

The above described data is sent to a preprocessing device 106, which is housed in a console outside the gantry 100 through a non-contact data transmitter 105. The preprocessing device 106 performs certain corrections such as sensitivity correction on the raw data. A storage device or data storing unit 112 then stores the resultant data that is also called projection data at a stage immediately before reconstruction processing. The storage device 112 is connected to a system controller 110 through a data/control bus, together with an image reconstruction unit or device 114, a display device 116, an input device 115, and a scan plan support apparatus 200. The scan plan support apparatus 200 includes a function for supporting an imaging technician to develop a scan plan.

According to one aspect of the current invention, one embodiment of the image reconstruction device 114 reconstructs an image from the projection data that is stored in the storage device 112 based upon a predetermined reconstruction process such as a filtered backprojection (FBP) technique. In another embodiment, the reconstruction device 114 optionally reconstructs an image from the projection data based upon a filtered backprojection (FBP) technique with an additional feature of emulating a specific iteration result at a predetermined number of iterations according to a predetermined iterative reconstruction algorithm. In general, the reconstruction device 114 generates a dense spectral image from the projection data that has been in a data pansharpening unit 117 according to the current invention.

The reconstruction device 114 is implemented in a combination of software and hardware and is not limited to a particular implementation. In the following description of the reconstruction device 114, the term, "unit" or "device" is inclusive of hardware and or software. Furthermore, the concept of the reconstruction device 114 is applicable to other modalities including nuclear medicine and magnetic resonance imaging (MRI).

One embodiment for pansharpening spectral data also includes a sonogram (raw data in the log domain after air calibration) or data pansharpening device or unit 117 according to the current invention. The data pansharpening unit 117 receives energy integration data that has been acquired at energy-integrating detectors as well as spectral energy data that has been acquired at photon-counting detectors which are less densely populated than the energy-integrating detectors. Furthermore, the data pansharpening unit 117 pansharpens the spectral energy data using the energy integration data to generate pansharpened spectral energy data according to a predetermined pansharpening algorithm. Finally, the reconstruction device 114 reconstructs at least one high resolution or dense spectral image based upon the pansharpened spectral energy data. In other words, the data pansharpening unit 117 receives the dense panchromatic data and at least one set of sparse spectral data and pansharpens at least the spectral data using the dense panchromatic data based upon a predetermined technique to generate dense spectral data as pansharpened data. In general, the predetermined technique involves a pansharpening algorithm that fuses dense information into sparse spectral data to generate dense spectral data to be used for generating a high-resolution spectral image.

Figure 2:
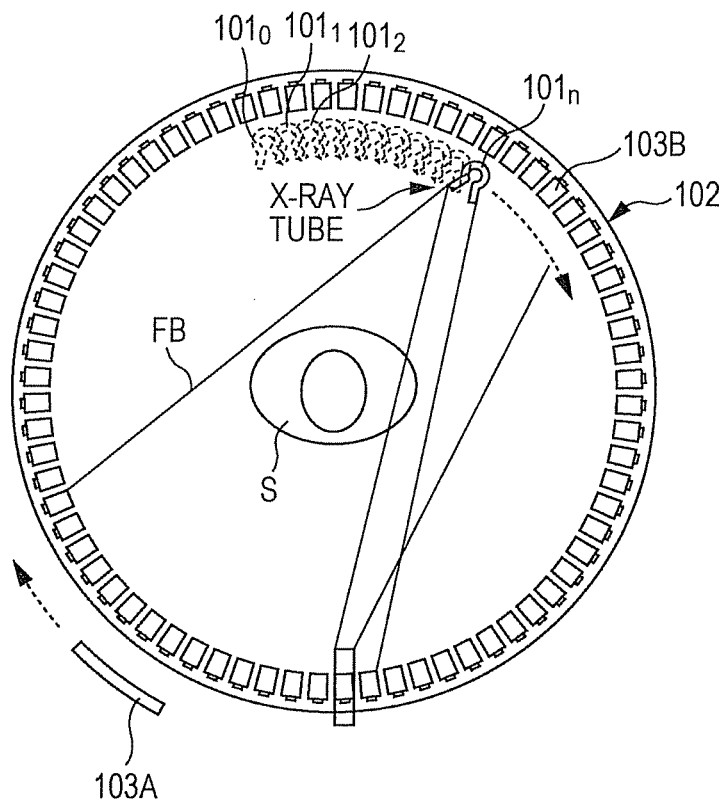
FIG. 2 is a diagram illustrating a partial diagram of the CT in one embodiment for pansharpening a sparse spectral data set according to the current invention.

Now referring to FIG. 2, a diagram illustrates a partial diagram of the CT in one embodiment for pansharpening a sparse spectral data set according to the current invention. The diagram illustrates the frame 102, on which a predetermined number of photon-counting detectors 103B are fixedly mounted in a sparse manner. Furthermore, an X-ray source 101 rotates along a predetermined path inside the sparsely placed photon-counting detectors 103B so that the sparsely placed photon-counting detectors 103B detect X-ray transmitted through the patient S. In a certain embodiment, an energy-integrating detector 103A is also diametrically placed from the X-ray source 101 across a patient S. The energy-integrating detector 103A is optionally located outside the photon-counting detectors 103B and rotates together with the X-ray source 101 as indicated by dotted arrows for detecting X-ray transmitted through the patient S and then reached through the gaps between the sparsely placed photon-counting detectors 103B. In certain embodiments, the X-ray source 101 projects X-ray in a predetermined fan beam while each of the photon-counting detectors 103B receives the X-ray transmitted from different positions such as at $101_0$, $101_1$, $101_2$ and $101_n$ as the X-ray source 101 rotates along a predetermined path.

Still referring to FIG. 2, the above described embodiments acquire data in the CT system for pansharpening at least a sparse spectral data set according to the current invention. In general, the X-ray source 101 generates polychromatic X-ray in a fan beam geometry in one embodiment according to the current invention. Furthermore, the energy-integrating detectors 103A generally have detector elements at a relatively high density with respect to those of the sparsely placed photon-counting detectors 103B. Although there is no specific limitation as to the number of the photon-counting detectors 103B, one embodiment has approximately one hundred photon-counting detectors along the circular path so ample space is left between the adjacent detectors for the X-ray to reach the energy-integrating detector 103A, which is has a high detector-element density and is located behind the photon-counting detectors 103B. Because of the sparsity, the photon-counting detectors 103B sample the views at a low sampling rate while each of the photon-counting detectors 103B experiences a relatively long sampling time for additional photon counts. Consequently, the photon-counting detectors 103B acquire sparse raw data. That is, the sparsely placed photon-counting detectors 103B acquire sparse spectral data while the energy-integrating detectors 103A acquire dense panchromatic (non-spectral) data. The above sparse and dense spectral data sets are used for pansharpening before a high-resolution spectral image is reconstructed.

Figure 3:
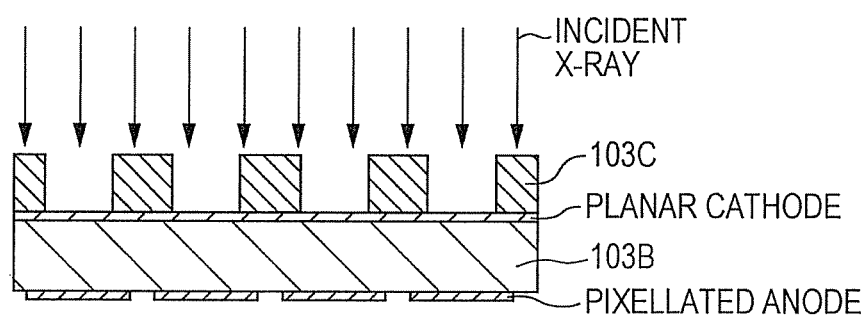
FIG. 3 is a diagram illustrating a cross sectional view of the photon-counting detectors 103B in one embodiment according to the current invention.

Now referring to FIG. 3, a diagram illustrates a cross sectional view of the photon-counting detectors 103B in one embodiment according to the current invention. In general, each of the photon-counting detectors 103B has a predetermined number of energy discriminating bins for separately counting a number of photons. The cross sectional diagram illustrates the photon-counting detector 103B with a collimator 103C that has been used in one embodiment of the pansharpening CT system according to the current invention. The collimator 103C is mounted on the surface of the photon-counting detector 103B for separating incident X-ray into certain individual detector surface areas as well as shielding certain other detector surface areas from receiving the X-ray. Each of the separated detector surfaces areas detects photon counts in a certain predetermined energy range. Thus, the on-detector collimator 103C defines individual detector channels or bins for establishing detector pixels.

Figure 4:
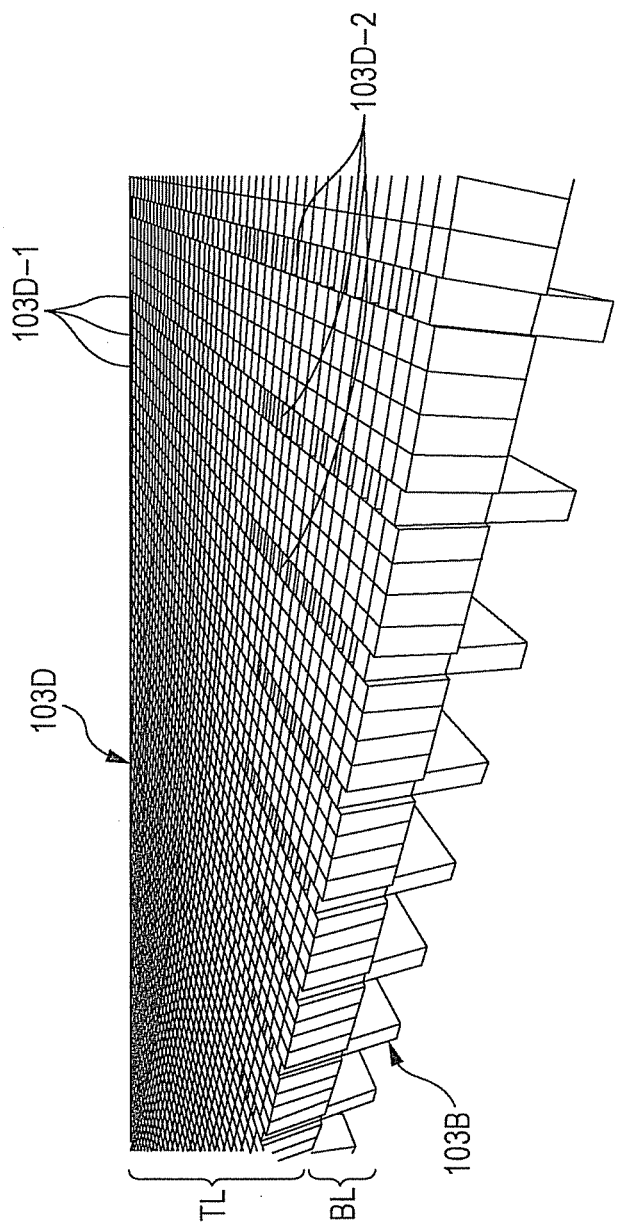
FIG. 4 is a diagram illustrating a prospective view of another embodiment of the detector 103 for acquiring data sets in the CT system for pansharpening at least a sparse spectral data set according to the current invention.

Now referring to FIG. 4, a diagram illustrates a prospective view of another embodiment of the detector 103 for acquiring data sets in the CT system for pansharpening at least a sparse spectral data set according to the current invention. The detector 103 further includes a top layer TL and a bottom layer BL and the top layer TL is located closer to the X-ray that has been transmitted through the subject than the bottom layer BL. In general, the top layer TL has the energy-integrating detector 103D, whose detector elements 13D-1 are adjacently placed in a densely manner as indicated by elongated cubes while the top layer TL is lacking these detector elements 13D-1 at predetermined locations or slits 103D-2. The slits 103D-2 of the top layer TL allows the X-ray to reach the bottom layer BL. The slits 103D-2 are configured at a predetermined interval and along a predetermined direction with respect to the energy-integrating detector elements 13D-1. In the bottom layer BL, there are a predetermined number of one-dimensional (1D) arrays of photon-counting detector 103B, each row of the arrays is optionally placed along a predetermined direction with respect to the slits 103D-2. In one implementation, the 1D array of the photon-counting detector 103B is placed directly underneath the top layer TL along a straight line of the intermittent slits 103D-2. Thus, the intermittent slits 103D-2 optionally configures pixilated photon-counting detector 103B in one implementation of the detector 103 for acquiring data sets in the CT system for pansharpening at least a sparse spectral data set according to the current invention.

The configurations as illustrated in FIGS. 1, 2, 3 and 4 are mere illustrations for implementing the parts of a photon-counting CT in one embodiment for pansharpening a sparse spectral data set based upon a dense panchromatic data set according to the current invention. To practice the current invention as recited in the claims, there are not necessarily specific requirements as to how the photon-counting detectors and the energy-integrating detector are employed to acquire sparse spectral data sets and dense panchromatic data sets. By the same token, there are not necessarily specific requirements as to how the sparse spectral data and the dense panchromatic data are acquired. Both of the data sets are either after log as in projection data or before log. Lastly, there are not necessarily specific requirements as to how sparse the photon-counting data should be with respect to the energy-integrating data.

In certain embodiments, the following exemplary features are implemented. For example, a first detector element size of the energy integrating detectors is substantially equal to a second detector element size of the photon counting detectors in one embodiment. In another embodiment, a first flux level in acquiring the spectral energy data is lower than a second flux level that is used for acquiring the energy integration data. In acquiring the spectral energy data and the energy integration data, two separate sources are respectively used in one embodiment while a single common source is used in another embodiment. In yet another embodiment, an image iteratively reconstructed using the dense spectral energy data as a seed.

Figure 5:
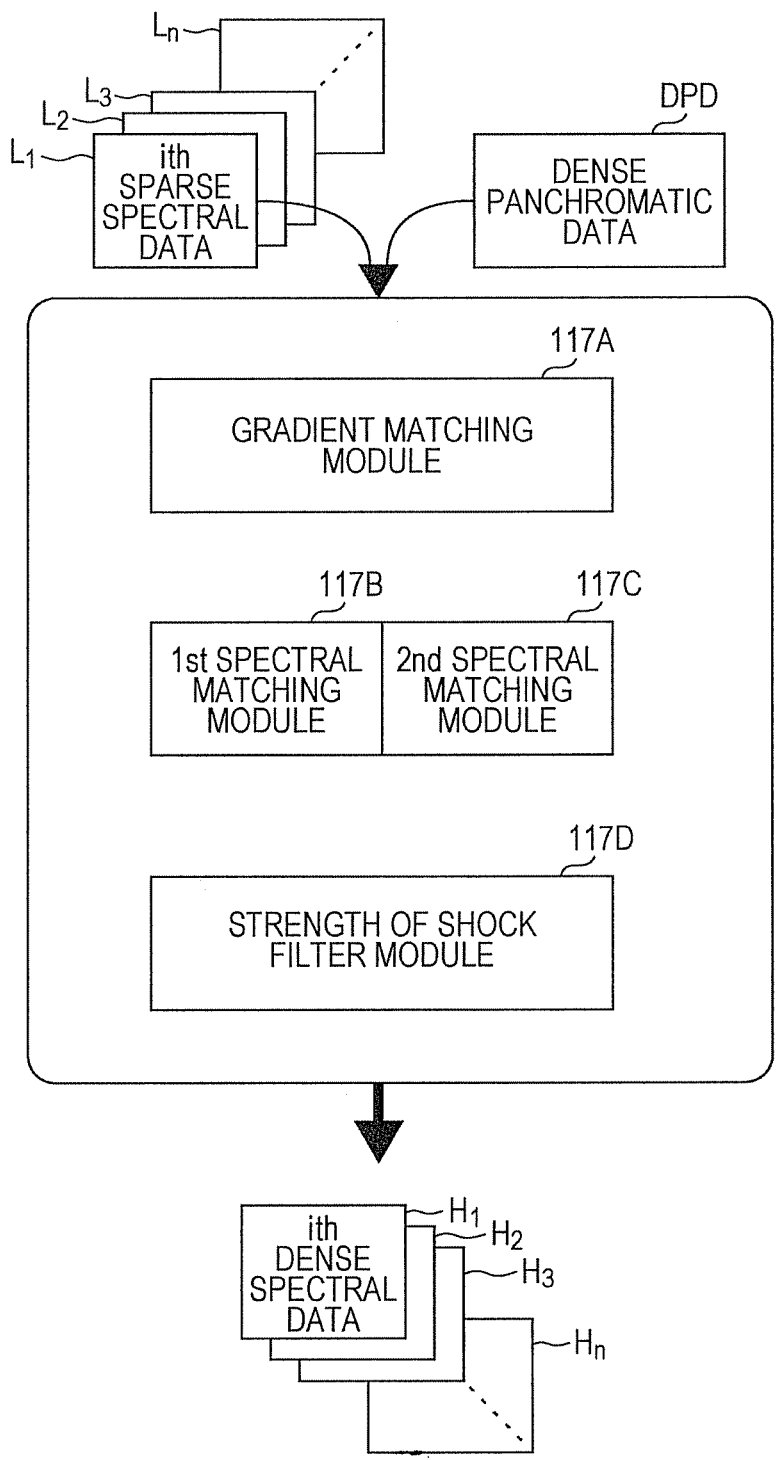
FIG. 5 is a diagram illustrating one embodiment of the sinogram or data pansharpening unit according to the current invention.

Now referring to FIG. 5, a diagram illustrates one embodiment of the sinogram or data pansharpening unit 117 according to the current invention. The data pansharpening unit 117 receives a predetermined number of data sets as inputs. In general, the data pansharpening unit 117 receives a set of sparse spectral energy data sets L1 through Ln, each corresponding to one of the predetermined bins of the photon-counting detectors. That is, each of the sparse data sets L1 through Ln has been acquired at a particular bin of the photon-counting detectors. For example, if the photon-counting detector has a predetermined number of n bins, n sparse data sets L1 through Ln have been acquired, and up to n sparse data sets are inputted into the data pansharpening unit 117 for being pansharpened to improve their data quality. At the same time, a single dense panchromatic energy integration data set DPD is also inputted into the data pansharpening unit 117. That is, the dense panchromatic data DPD has been acquired at an energy-integrating detector. The data pansharpening unit 117 outputs a set of pansharpened spectral data sets H1 through Hn, each corresponding to one of the predetermined bins of the photon-counting detectors.

Still referring to FIG. 5, the data pansharpening unit 117 further includes a gradient matching module 117A, a first spectral matching module 117B and a second spectral matching module 117C for ultimately outputting a set of pansharpened spectral data sets H1 through Hn. In addition, the data pansharpening unit 117 optionally includes a strength shock filter module 117D. In one implementation, at least some of the gradient matching module 117A, the spectral matching modules 117B, 117C and the strength shock filter module 117D are implemented as software modules. In another implementation, at least some of the gradient matching module 117A, the spectral matching modules 117B, 117C and the strength shock filter module 117D are implemented as a combination of software modules and hardware devices. To practice the current invention, additional requirements are not necessarily needed other than those as recited in the claims as to how the gradient matching module 117A, the spectral matching modules 117B, 117C and the strength shock filter module 117D are implemented.

In general, the gradient matching module 117A, the first spectral matching module 117B and the second spectral matching module 117C are implemented based upon a predetermined algorithm as described by a predetermined equation such as Equation (1) below:

$$E(g_i) = \lambda_1 E_{gradient}(g_i) + \lambda_2 E_{radiometric}(g_i) + \lambda_3 E_{correlation}(g_i) = \qquad (1)$$
$$\lambda_1 \int_\Omega |\nabla g_i - \alpha(\nabla D_{pan})\nabla D_{pan}|^2 dx +$$
$$\lambda_2 \sum_{j=1}^n \int_\Omega (g_j^2 - M_j^2)^2 dx + \lambda_3 \sum_{j=1}^n \int_\Omega (g_i M_j - g_j M_i)^2 dx$$

Wherein $\alpha$ is a predetermined coefficient, $M_i$ is one of sparse spectral data sets, $D_{pan}$ is a panchromatic dense data set, and $g_i$ is a corresponding one of the pansharpened spectral data sets. That is, $g_i$ is an objective functional to be minimized for optimization. Furthermore, an omega symbol just means the area to integrate over, and the whole data is integrated in the above case. $g_i$ is summed over all j or all the data sets to include information from the other spectral data sets to substantially improve the quality of data set $g_i$, the objective functional.

In one embodiment of the data pansharpening unit 117, the gradient matching module 117A performs the first term for resolution recovery as described in Equation (2), $$\lambda_1 \int_\Omega |\nabla g_i - \alpha(\nabla D_{pan})\nabla D_{pan}|^2 dx \qquad (2)$$

which encourages the injection of details from the panchromatic dense data set. A predetermined first coefficient value $\lambda 1$ weighs the radient matching term for density recovery and has a range between 0 and 1.

By the same token, the first spectral matching module 117B performs the second term for keeping gray levels faithful to the sparse data sets as described in Equation (3), $$\lambda_2 \sum_{j=1}^n \int_\Omega (g_j^2 - M_j^2)^2 dx \qquad (3)$$

which enforces matching of spectral characteristics with the multispectral data sets. The second term just matches the sparseness and the denseness for one data set at a time and then sums over all data sets. A predetermined second coefficient value $\lambda 2$ weighs the spectral matching term for keeping gray levels faithful to the sparse data sets and has a range between 0 and 1.

Optionally, the second spectral matching module 117C performs the second term for keeping gray levels faithful to the sparse data sets as described in Equation (4), $$\lambda_3 \sum_{j=1}^n \int_\Omega (g_i M_j - g_j M_i)^2 dx \qquad (4)$$

which enforces matching of spectral characteristics with the multispectral data sets. The third term is called a correlation term that matches different levels in sparseness. For example, the first spectral bin is matched with the second spectral bin. In any case, both the first spectral matching module 117B and the second spectral matching module 117C substantially keep gray levels faithful to the dense panchromatic data set. A predetermined third coefficient value $\lambda 3$ weighs the spectral matching term for keeping gray levels faithful to the sparse data sets and has a range between 0 and 1.

In this regard, another embodiment of the data pansharpening unit 117 fails to include or deactivates the second spectral matching module 117C so that the data pansharpening unit 117 only includes the gradient matching module 117A and the first spectral matching module 117B. By deriving a first variation of the above functional, it is optionally minimized with a standard gradient descent algorithm as described in Equation (5).

$$E(g_i) = \lambda_1 \int_\Omega \|\nabla g_i - \alpha(\nabla D_{pan})\|^2 dx dy + \lambda_2 \int_\Omega (g_i - M_i)^2 dx dy \qquad (5)$$

To reiterate some of the notations, $M_i$ is one of spectral sparse data sets, $D_{pan}$ is a panchromatic dense data set, and $g_i$ is a corresponding one of the pansharpended spectral data sets. That is, $g_i$ is an objective functional to be minimized for optimization.

Yet in another embodiment, the strength shock filter module 117D optionally performs the following term for promoting sharpening of a data set as described in Equation (6), $$\lambda_4 |\nabla g_i^k| sign(\Delta g_i^k) dx \qquad (6)$$

The above term is called an inverse diffusion term for sharpening a data set in an updating equation such as steepest descent as shown in Equation (7). A predetermined fourth coefficient value $\lambda 4$ weighs the inverse diffusion term for the strength of the shock filter and has a range between 0 and 1.

$$g_i^{k+1} - g_i^k / \Delta t = \qquad (7)$$
$$-2\lambda_1 (div(\alpha(\nabla D_{pan})\nabla D_{pan}) - \Delta g_i^k) - 4\lambda_2 \sum_{j=1}^n ((g_j^k)^2 - M_j^2)g_i^k -$$
$$2\lambda_3 \sum_{j=1}^n (g_j^k M_j - g_j^k M_i)M_j - \lambda_4 |\nabla g_i^k| sign(\Delta g_i^k)$$

The above four predetermined coefficients $\lambda 1$ through $\lambda 4$ are used to weigh the relative emphasis among the four competing terms of the gradient matching module 117A, the first spectral matching module 117B, the second spectral matching module 117C and the strength shock filter module 117D for ultimately outputting a set of dense spectral data sets H1 through Hn. A sum of the coefficients $\lambda 1$ through $\lambda 4$ equals to one in one embodiment. Other embodiments of the data pansharpening unit 117 are not limited to the above described modules and optionally include other modules. In any case, the embodiments are implemented in a variety of ways to control these modules so that some or all of the modules are optionally operated in parallel.

Figure 6:
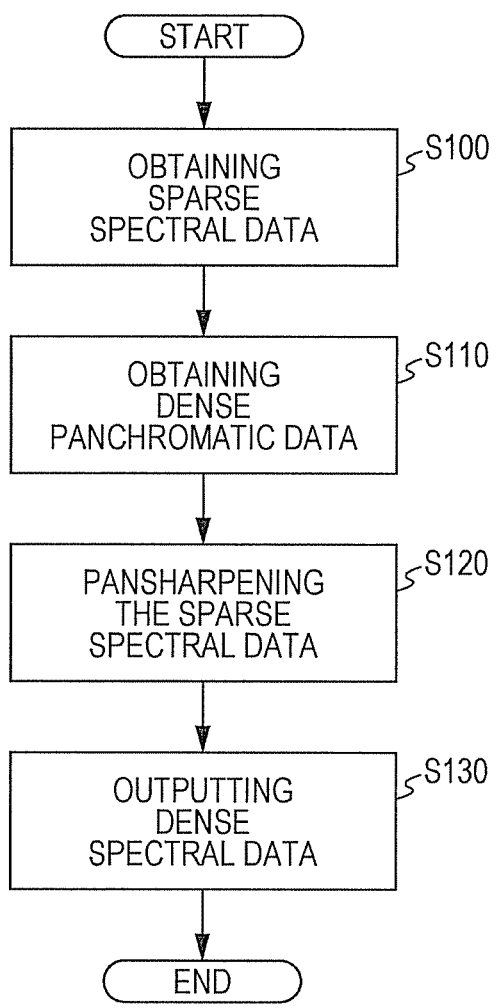
FIG. 6 is a flow chart illustrating steps or acts involved in an exemplary process of pansharpening sparse spectral energy data to generate pansharpened spectral energy data based upon at least one dense panchromatic energy integration data according to the current invention.

Now referring to FIG. 6, a flow chart illustrates steps or acts involved in an exemplary process of pansharpening sparse spectral energy data to generate pansharpened spectral energy data based upon at least one dense panchromatic energy integration data according to the current invention. The exemplary process merely illustrates certain steps that are optionally combined into a single step or that are optionally further divided into sub-steps. To perform the current invention, the exemplary process is not necessarily limited to the illustrated steps or acts. In addition, each of the steps and acts does not necessarily correspond to a single unit or device and is optionally performed by more than a single unit or device.

Still referring to FIG. 6, sparse spectral images are obtained in a step S100. In one embodiment, a predetermined number of sparse spectral energy data sets is reconstructed from corresponding spectral bin data that is initially acquired at certain photon-counting detectors such as CdTe/CdZnTe detectors. Although the sparse spectral energy data sets are acquired at the photon-counting detectors in the embodiment, there are no limitations as to how the sparse spectral energy data sets are obtained in the step S100 so long as these data sets are available for pansharpening.

By the same token, at least one dense panchromatic data set is obtained in a step S110. In one embodiment, at least one dense panchromatic data set is initially acquired at certain energy-integrating detectors. There are no limitations as to how the dense panchromatic data set is obtained in the step S110 so long as the data set is available for pansharpening. Furthermore, the chronological sequence of the steps S100 and S110 is irrelevant to the claimed invention. In this regard, the steps S100 and S110 are optionally performed in parallel in the claimed invention.

Still referring to FIG. 6, after a plurality of the sparse spectral energy data sets and at least the one dense panchromatic data set have been obtained, each of the sparse spectral energy data sets is pansharpened according to a predetermined technique such as one of the above algorithms based upon the dense panchromatic data set as well as other sparse spectral energy data sets in a step S120. The pansharpening step S120 is not limited to a particular algorithm and possibly includes other variations of the above described pansharpening algorithms. According to one embodiment, one exemplary algorithm is performed by a certain combination of the gradient matching module 117A, the first spectral matching module 117B, the second spectral matching module 117C and the strength shock filter module 117D as illustrated in FIG. 4 for ultimately outputting a set of dense spectral energy data sets H1 through Hn. The gradient matching module 117A, the first spectral matching module 117B, the second spectral matching module 117C and the strength shock filter module 117D respectively perform the various aspects of the pansharpening step S120 as described by Equations (2), (3), (4) and (6).

Because of the above described features of the exemplary process, multiple sets of the pansharpened spectral energy data sets are optionally obtained based upon the selected pansharpening techniques. Furthermore, each of the dense spectral energy data sets is optionally obtained based upon a selected pansharpening technique according to particular needs in the region of interest (ROI). In other words, the selected pansharpening technique is not necessarily identical in pansharpening the multiple sparse spectral energy data sets in the step S120.

As a result of the data pansharpening step S120, the dense spectral energy data sets are outputted in a step S130 according to the current invention. The outputting step S130 is optionally sequential as one object functional $g_i$ is minimized and the corresponding dense spectral data set is outputted in one exemplary process. In another exemplary process, the outputting step S130 waits till all of the dense spectral energy data sets are obtained. In any case, each of the dense spectral energy data sets is outputted for use at the end of outputting step 130.

Figure 7:
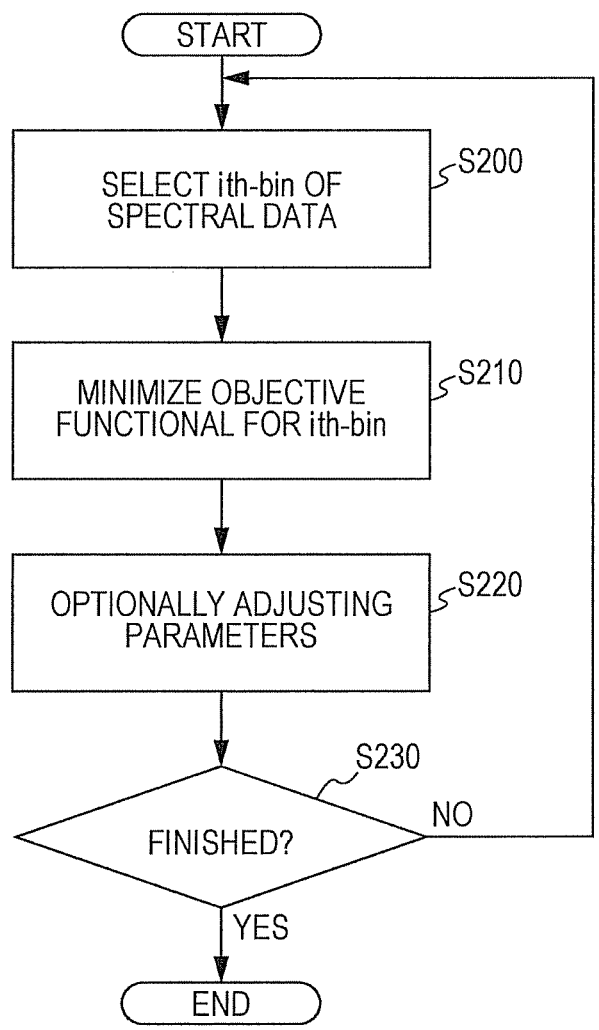
FIG. 7 illustrates more detailed aspects of the pansharpening step in one exemplary process according to the current invention.

After generally described with respect to the sinogram pansharpening step S120 in FIG. 6, more detailed aspects of the pansharpening step S120 are further illustrated in FIG. 7 in one exemplary process according to the current invention. In one exemplary process, the pansharpening step S120 further includes a step S200 of selecting ith bin of the spectral data, a step S210 of minimizing an object functional, a step S220 of optionally adjusting parameters or weights and a step of determining as to whether or not every sparse spectral energy data set is pansharpened.

Still referring to FIG. 7, the selecting bin step S200 selects a sparse spectral energy data set corresponding to the ith bin of the spectral data that has been acquired at a predetermined photon-counting detector. In one embodiment, the ith bin is sequentially selected from 1 through nth bin by incrementing an index i by one. In another embodiment, the ith bin is optionally selected by a user based certain spectral information with respect to a particular material basis. For example, the five spectral energy data sets are acquired by the photon-counting detectors with 5 bins.

In the minimizing step S210, the objective functional is minimized for the selected sparse spectral image corresponding to the ith bin of the spectral data. As described above, the pansharpened spectral energy data sets are found by minimizing the energy functional such as Equation (5) in one embodiment. In general, the use of pansharpening technique is computationally efficient than the use of an iterative technique for improving the sparse spectral energy data sets. On the other hand, the use of pansharpening technique is optionally combined with the use of an iterative technique in an alternative embodiment.

In the parameter adjusting step S220, certain predetermined parameters are optionally adjusted to further improve the quality of the spectral energy data sets during the sinogram pansharpening process according to the current invention. The optional parameters include the weights such as $\lambda 1$, $\lambda 2$, $\lambda 3$ and $\lambda 4$ as well as a as illustrated in Equation (1). In this regard, $\alpha$ is a predetermined coefficient. The predetermined first coefficient value $\lambda 1$ weighs the gradient matching term for resolution recovery and has an exemplary value of 0.1, 0.25, 0.5, 0.75 or 1.0. The predetermined second coefficient value $\lambda 2$ weighs the spectral matching term for keeping gray levels faithful to sparse spectral energy data sets and has an exemplary value of 0.1, 0.25, 0.5, 0.75 or 1.0. The predetermined third coefficient value $\lambda 3$ weighs the spectral matching term for keeping gray levels faithful to sparse spectral energy data sets and has an exemplary value of 0.1, 0.25, 0.5, 0.75 or 1.0. The parameter values are often empirically adjusted based upon the user input.

Lastly, it is determined as to whether or not the data pansharpening process should be terminated according to the current invention. That is, it is generally determined whether or not every one of the sparse spectral energy data sets of interest has been pansharpened according to a predetermined technique in the steps S200 through S210. If it is determined in the step S230 that every one of the sparse spectral energy data sets has been pansharpened, the exemplary pansharpening process terminates itself. On the other hand, if it is determined in the step S230 that not every one of the sparse spectral energy data sets has been pansharpened, the exemplary pansharpening process continues by repeating from the selecting step S200.

Figure 8A:
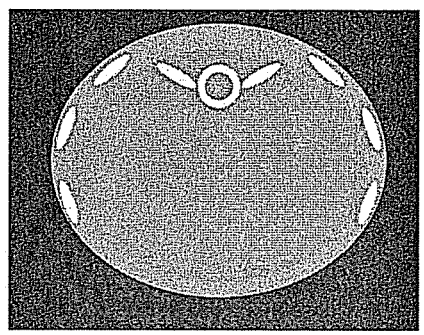
FIG. 8A is a 512×512 true image or a high-resolution spectral image that has been reconstructed from a full view of spectral data which has been acquired at a certain photon-counting detector of the CT system.

Now referring to FIGS. 8A, 8B, 8C and 8D, images illustrate an exemplary result of a pansharpened image according to the current invention. FIG. 8A is a 512×512 true image or a high-resolution spectral image that has been reconstructed from a full view of spectral data which has been acquired at a certain photon-counting detector of the CT system. Although a single true image is illustrated in the example, a plurality of the spectral images is optionally generated. The high-resolution spectral image has been reconstructed based upon a predetermined reconstruction algorithm using a full view of the data at the photon counting detectors.

Figure 8B:
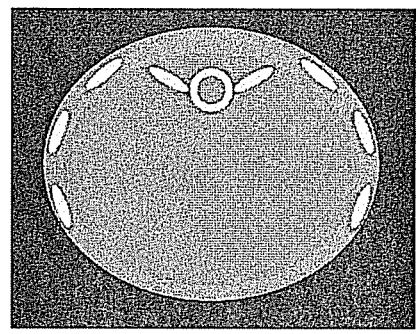
FIG. 8B is a 512×512 high-resolution or pansharpened spectral image of the same predetermined phantom that has been generated from the high-resolution panchromatic image and the low-resolution spectral image based upon a predetermined image-domain pansharpening technique.

FIG. 8B is a 512×512 high-resolution or pansharpened spectral image of the same predetermined phantom that has been generated from the high-resolution panchromatic image and the low-resolution spectral image based upon a predetermined image-domain pansharpening technique. The high-resolution pansharpened spectral image has been generated based upon a predetermined pansharpening algorithm which is selected from a group of pansharpening algorithms. The pansharpened spectral image as illustrated has substantially improved its resolution over unprocessed low-resolution spectral image while it maintains its spectral characteristics.

Figure 8C:
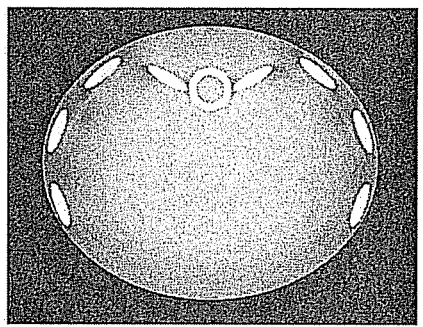
FIG. 8C is a 512×512 integrating image or a high-resolution panchromatic image of a predetermined phantom that has been reconstructed from non-spectral data which has been acquired at a certain energy-integrating detector of the CT system.

FIG. 8C is a 512×512 integrating image or a high-resolution panchromatic image of a predetermined phantom that has been reconstructed from non-spectral data which has been acquired at a certain energy-integrating detector of the CT system. Although a single image is illustrated in the example, a plurality of the dense panchromatic images is optionally generated. The integrating image has been reconstructed based upon a predetermined reconstruction algorithm using a full view of the data at the energy integrating detectors.

Figure 8D:
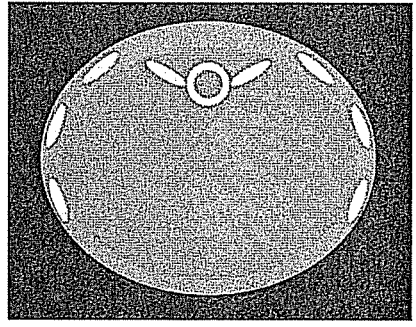
FIG. 8D is a 512×512 high-resolution sinogram restoration image of the same predetermined phantom that has been generated from pansharpened spectral data using the dense panchromatic data and the sparse spectral energy data based upon a predetermined data-domain pansharpening technique.

FIG. 8D is a 512×512 high-resolution sinogram restoration image of the same predetermined phantom that has been generated from pansharpened spectral data using the dense panchromatic data and the sparse spectral energy data based upon a predetermined data-domain pansharpening technique. The pansharpened spectral data has been generated based upon a predetermined data pansharpening algorithm which is selected from a group of data pansharpening algorithms. The sinogram restoration image as illustrated has substantially improved its resolution over unprocessed low-resolution spectral image while it maintains its spectral characteristics.

Now referring to FIGS. 9A, 9B, 9C and 9D, a region of interest (ROI) is substantially improved based upon a predetermined data pansharpening technique in the CT system according to the current invention. One of the exemplary phantoms represents an axial slice through the abdomen and contains ellipses made of bone, liver, water and muscle. In general, the pansharpened spectral energy data sets from each of the energy bins of the photon counting detector have substantially recovered nearly all of the resolution of the ground-truth or the dense panchromatic image with some minor exceptions of spectral distortion in the high contrast objects. FIG. 9 illustrate the improvement in a particular ROI using spectral data from a particular bin at 135 kVP in the sparse image from a particular energy bin.

Figure 9A:
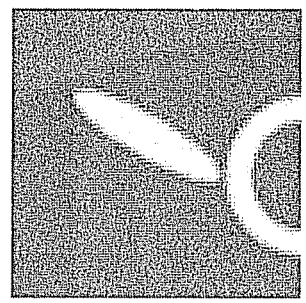
FIG. 9A is a 512×512 true image or a high-resolution spectral image in a region of interest (ROI) that has been reconstructed from a full view of spectral data which has been acquired at a certain photon-counting detector of the CT system.

FIG. 9A is a 512×512 true image or a high-resolution spectral image in a region of interest (ROI) that has been reconstructed from a full view of spectral data which has been acquired at a certain photon-counting detector of the CT system. Although a single true image is illustrated in the example, a plurality of the spectral images is optionally generated. The high-resolution spectral image has been reconstructed based upon a predetermined reconstruction algorithm using a full view of the data at the photon counting detectors.

Figure 9B:
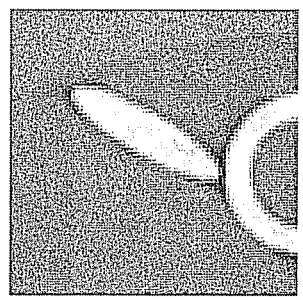
FIG. 9B is a 512×512 high-resolution or pansharpened spectral image in the corresponding region of interest (ROI) of the same predetermined phantom that has been generated from the high-resolution panchromatic image and the low-resolution spectral image based upon a predetermined image-domain pansharpening technique.

FIG. 9B is a 512×512 high-resolution or pansharpened spectral image in the corresponding region of interest (ROI) of the same predetermined phantom that has been generated from the high-resolution panchromatic image and the low-resolution spectral image based upon a predetermined image-domain pansharpening technique. The high-resolution pansharpened spectral image has been generated based upon a predetermined pansharpening algorithm which is selected from a group of pansharpening algorithms. The pansharpened spectral image as illustrated has substantially improved its resolution over unprocessed low-resolution spectral image while it maintains its spectral characteristics.

Figure 9C:
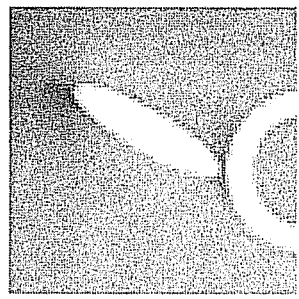
FIG. 9C is a 512×512 integrating image or a high-resolution panchromatic image in the corresponding region of interest (ROI) of the same predetermined phantom that has been reconstructed from non-spectral data which has been acquired at a certain energy-integrating detector of the CT system.
Figure 9D:
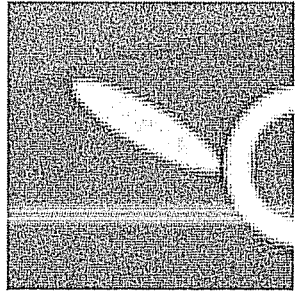
FIG. 9D is a 512×512 high-resolution sinogram restoration image in the corresponding region of interest (ROI) of the same predetermined phantom that has been generated from pansharpened spectral data using the dense panchromatic data and the sparse spectral energy data based upon a predetermined data-domain pansharpening technique.

FIG. 9C is a 512×512 integrating image or a high-resolution panchromatic image in the corresponding region of interest (ROI) of the same predetermined phantom that has been reconstructed from non-spectral data which has been acquired at a certain energy-integrating detector of the CT system. Although a single image is illustrated in the example, a plurality of the dense panchromatic images is optionally generated. The integrating image has been reconstructed based upon a predetermined reconstruction algorithm using a full view of the data at the energy FIG. 9D is a 512×512 high-resolution sinogram restoration image in the corresponding region of interest (ROI) of the same predetermined phantom that has been generated from pansharpened spectral data using the dense panchromatic data and the sparse spectral energy data based upon a predetermined data-domain pansharpening technique. The pansharpened spectral data has been generated based upon a predetermined data pansharpening algorithm which is selected from a group of data pansharpening algorithms. The sinogram restoration image as illustrated has substantially improved its resolution over unprocessed low-resolution spectral image while it maintains its spectral characteristics.

Now referring to FIG. 10, a pair of graphs depicts how an exemplary pansharpening process according to the current invention affects material classification. Using a predetermined material classification phantom containing disks of various iodine and calcium concentrations, an exemplar pan-sharpening process fails to affect material classification tasks as depicted by the scatter plots from ROI's in the different disks. From the scatter plots, material classification is largely unaffected by the exemplary pansharpening process according to the current invention.

Figure 10A:
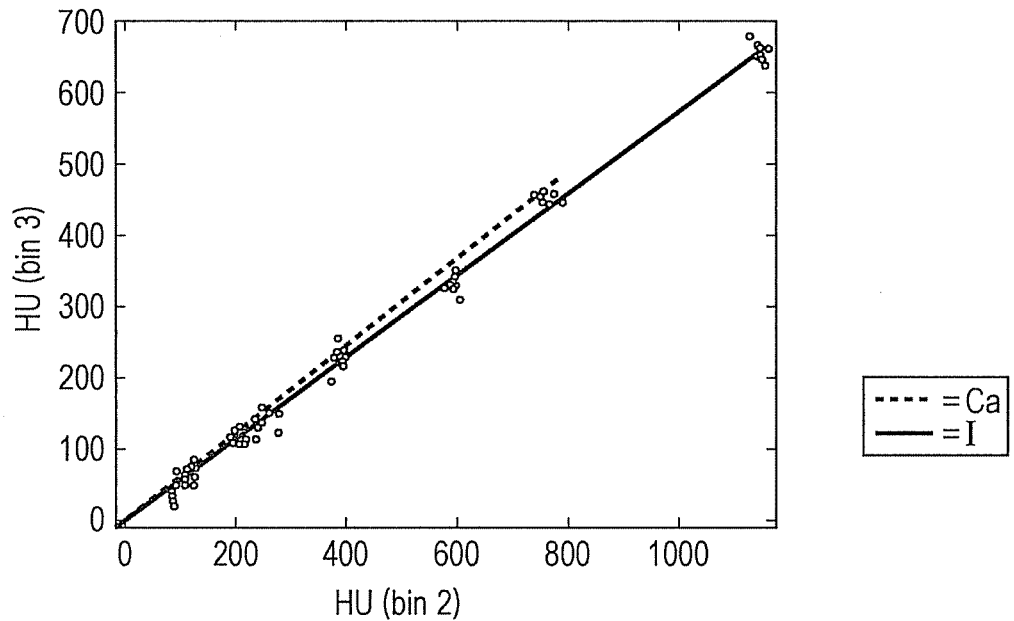
FIG. 10A is a scatter plot depicting material classification of calcium and iodine with an angler separation of 3.5 degrees in the dense pansharpened spectral data set.

Now referring to FIG. 10A, the scatter plot depicts material classification of calcium and iodine with an angler separation of 3.5 degrees in the dense pansharpened spectral data set. The x axis is a HU value in the third energy bin while the y axis is a HU value in the fourth energy bin. Furthermore, a dotted line indicates calcium while a dotted line indicates calcium. Both the material classifications of calcium and iodine are substantially linear between the third and fourth bins in the dense pansharpened spectral data set after the exemplary pansharpening process according to the current invention.

Figure 10B:
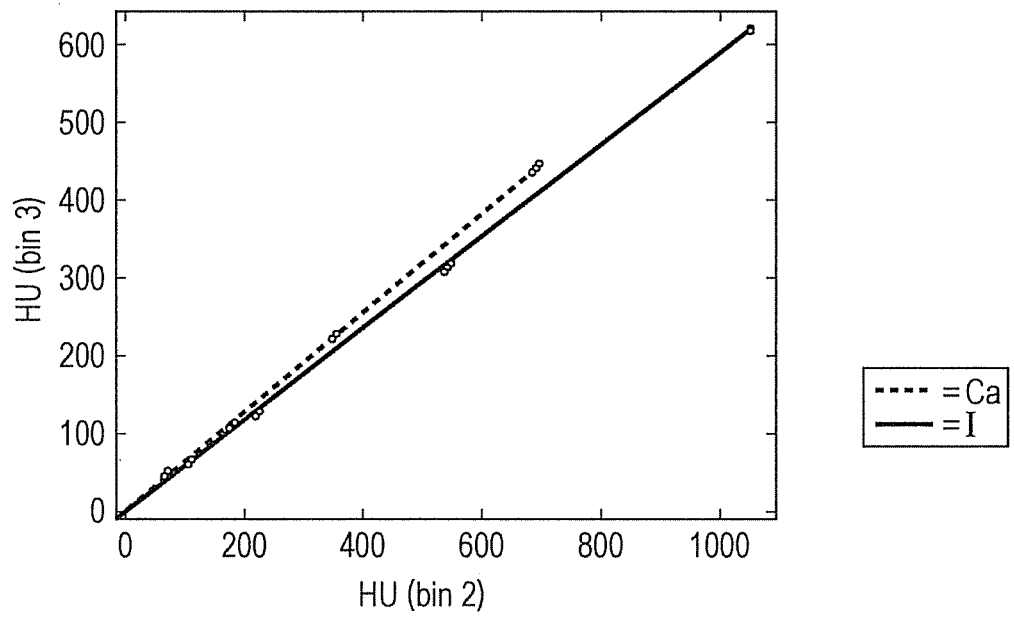
FIG. 10B is a scatter plot depicting material classification of calcium and iodine with an angler separation of 3.3 degrees in the dense panchromatic data set.

Now referring to FIG. 10B, the scatter plot depicts material classification of calcium and iodine with an angler separation of 3.3 degrees in the dense panchromatic data set. The x axis is a HU value in the third energy bin while the y axis is a HU value in the fourth energy bin. Furthermore, a dotted line indicates calcium while a dotted line indicates calcium. Both the material classifications of calcium and iodine are substantially linear between the third and fourth bins in dense panchromatic data set before the exemplary pansharpening process according to the current invention. As a result of comparison between the two scatter plots in FIGS. 10A and 10B, material classification of calcium and iodine is largely unaffected the third and fourth bins by the exemplary pansharpening process according to the current invention.

It is to be understood, however, that even though numerous characteristics and advantages of the present invention have been set forth in the foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

What is claimed is:

1. A method of improving a spectral image, comprising;
   acquiring dense energy integration data at energy-integrating detectors;
   acquiring sparse spectral energy data at photon-counting detectors that are sparsely populated with respect to the energy-integrating detectors, each of the photon-counting detectors experiencing a sufficient sampling time for additional photon counts at a low sampling rate due to the sparsity of the photon-counting detectors to generate the sparse spectral energy data;
   pansharpening a first sinogram of the sparse spectral energy data using a second sinogram of the dense energy integration data to generate a third sinogram of dense pansharpened spectral energy data according to a predetermined pansharpening algorithm; and
   reconstructing at least one high resolution spectral image based upon the third sinogram of the dense pansharpened spectral energy data, wherein said pansharpening uses a predetermined algorithm as described by $E(g_i)=\lambda_1\int_\Omega \|\nabla g_i - \alpha(\nabla D_{pan})\|^2 dxdy + \lambda_2 \int_\Omega (g_i - M_i)^2 dxdy$ where $D_{pan}$ is the dense energy integration data, $M_i$ is the i'th channel of sets of sparse multispectral energy data sets, and $g_i$ is the i'th channel of sets of the dense pansharpened spectral energy data, E is minimizing energy functional, $\alpha$ is a predetermined coefficient, $\lambda_1$ is predetermined first coefficient value for weighing a gradient matching term for resolution recovery, $\lambda_2$ is predetermined second coefficient value for keeping gray level faithful, $\Omega$ just means an overall detector area to integrate over, $\nabla$ is gradient, x is a detector location along a predetermined x axis, y is a detector location along a predetermined y axis.

2. The method of improving a spectral image according to claim 1 wherein the photon counting detectors are sparsely fixed along a predetermined trajectory path.

3. The method of improving a spectral image according to claim 1 wherein a first detector element size of the energy integrating detectors is substantially equal to a second detector element size of the photon counting detectors.

4. The method of improving a spectral image according to claim 1 wherein said acquiring the sparse spectral energy data utilizes a first flux level that is lower than a second flux level that is used for said acquiring the dense energy integration data.

5. The method of improving a spectral image according to claim 1 wherein said acquiring the sparse spectral energy data and said acquiring the dense energy integration data utilize two separate sources.

6. The method of improving a spectral image according to claim 1 wherein said acquiring the sparse spectral energy data and said acquiring the dense energy integration data utilize a single common source.

7. The method of improving a spectral image according to claim 1 further comprising an additional step of iteratively reconstructing an image using the dense pansharpened spectral energy data as a seed.

8. The method of improving a spectral image according to claim 1 wherein a collimator is mounted on a surface of each of the photon-counting detectors for separating incident X-ray into certain individual detector surface areas as well as shielding certain other detector surface areas from receiving the X-ray.

9. A system for improving a spectral image, comprising;
   energy integrating detectors for acquiring dense energy integration data;
   photon counting detectors that are sparsely populated with respect to said energy integrating detectors for acquiring sparse spectral energy data, each of the photon-counting detectors experiencing a sufficient sampling time for additional photon counts at a low sampling rate due to the sparsity of the photon-counting detectors to generate the sparse spectral energy data;
   a data storing circuit for storing the dense energy integration data and the sparse spectral energy data;
   a data pansharpening circuit connected to said data storing circuit for pansharpening a first sinogram of the sparse spectral energy data using a second sinogram of the dense energy integration data to generate a third sinogram of dense pansharpened spectral energy data; and
   an image reconstruction circuit connected to said data storing circuit and said data pansharpening circuit for reconstructing at least a high resolution spectral image from the third sinogram of the dense pansharpened spectral energy data and the dense energy integration data wherein said data pansharpening circuit for pansharpening according to a predetermined algorithm as described by $E(g_i)=\lambda_1\int_\Omega \|\nabla g_i - \alpha(\nabla D_{pan})\|^2 dxdy + \lambda_2 \int_\Omega (g_i - M_i)^2 dxdy$
   where $D_{pan}$ is the dense energy integration data, $M_i$ is the i'th channel of sets of sparse multispectral energy data, and $g_i$ is the i'th channel of the pansharpened spectral energy data, E is minimizing energy functional, $\alpha$ is a predetermined coefficient, $\lambda_1$ is predetermined first coefficient value for weighing a gradient matching term for resolution recovery, $\lambda_2$ is predetermined second coefficient value for keeping gray level faithful, $\Omega$ just means an overall detector area to integrate over, $\nabla$ is gradient, x is a detector location along a predetermined x axis, y is a detector location along a predetermined y axis.

10. The system for improving a spectral image according to claim 9 wherein said photon counting detectors are sparsely fixed along a predetermined trajectory path.

11. The system for improving a spectral image according to claim 9 further comprising a single source for said energy integrating detectors and said photon counting detectors.

12. The system for improving a spectral image according to claim 9 wherein said photon counting detectors have a first detector element size that is substantially equal to a second detector element size of said energy integrating detectors.

13. The system for improving a spectral image according to claim 9 wherein said photon counting detectors utilize a first flux level that is lower than a second flux level that is used for said energy integration detectors.

14. The system for improving a spectral image according to claim 9 wherein said image reconstruction circuit iteratively reconstructs an image using the dense pansharpened spectral energy data set as a seed.

15. The system for improving a spectral image according to claim 9 wherein a collimator is mounted on a surface of each of the photon-counting detectors for separating incident X-ray into certain individual detector surface areas as well as shielding certain other detector surface areas from receiving the X-ray.

16. A system for improving a spectral image, comprising:
energy integrating detectors in a first predetermined detector size for acquiring dense energy integration data;
photon counting detectors that are sparsely populated with respect to said energy integrating detectors for acquiring sparse spectral energy data, each of the photon-counting detectors experiencing a sufficient sampling time for additional photon counts at a low sampling rate due to the sparsity of the photon-counting detectors to generate the sparse spectral energy data;
a data storing circuit for storing the dense energy integration data and the sparse spectral energy data;
a data pansharpening circuit connected to said data storing circuit for pansharpening a first sinogram of the sparse spectral energy data using a second sinogram of the dense energy integration data to generate a third sinogram of dense pansharpended spectral energy data; and
an image reconstruction circuit connected to said data storing circuit and said data pansharpening circuit for reconstructing at least a high resolution spectral image from the third sinogram of the dense pansharpened spectral energy data and the dense energy integration data wherein said data pansharpening circuit for pansharpening according to a predetermined algorithm as described by $E(g_i) = \lambda_1 \int_\Omega \|\nabla g_i - \alpha(\nabla D_{pan})\|^2 dxdy + \lambda_2 \int_\Omega (g_i - M_i)^2 dxdy$
where $D_{pan}$ is the dense energy integration data, $M_i$ is the i'th channel of sets of sparse multispectral energy data, and $g_i$ is the i'th channel of the pansharpened spectral energy data, E is minimizing energy functional, $\alpha$ is a predetermined coefficient, $\lambda_1$ is predetermined first coefficient value for weighing a gradient matching term for resolution recovery, $\lambda_2$ is predetermined second coefficient value for keeping gray level faithful, $\Omega$ just means an overall detector area to integrate over, $\nabla$ is gradient, x is a detector location along a predetermined x axis, y is a detector location along a predetermined y axis.

17. The system for improving a spectral image according to claim 16 wherein a collimator is mounted on a surface of each of the photon-counting detectors for separating incident X-ray into certain individual detector surface areas as well as shielding certain other detector surface areas from receiving the X-ray.

* * * * *